(12) United States Patent
Bauer

(10) Patent No.: US 10,159,589 B2
(45) Date of Patent: Dec. 25, 2018

(54) KNEE BRACE

(71) Applicant: medi GmbH & Co. KG, Bayreuth (DE)

(72) Inventor: Patrick Bauer, Auerbach (DE)

(73) Assignee: MEDI GMBH & CO. KG, Bayreuth (DE)

( * ) Notice: Subject to any disclaimer, the term of this patent is extended or adjusted under 35 U.S.C. 154(b) by 406 days.

(21) Appl. No.: 14/717,102

(22) Filed: May 20, 2015

(65) Prior Publication Data

US 2015/0335457 A1 Nov. 26, 2015

(30) Foreign Application Priority Data

May 22, 2014 (DE) .................. 10 2014 107 239

(51) Int. Cl.
    *A61F 5/01*     (2006.01)
    *A61F 5/30*     (2006.01)

(52) U.S. Cl.
    CPC .......... *A61F 5/0123* (2013.01); *A61F 5/0109* (2013.01); *A61F 5/30* (2013.01); *A61F 2005/0146* (2013.01); *A61F 2005/0172* (2013.01); *A61F 2005/0176* (2013.01)

(58) Field of Classification Search
    CPC ........ A61F 5/01; A61F 5/0123; A61F 5/0102; A61F 5/30; A61F 5/0125; A61F 2005/0139; A61F 2005/0146; A61F 2005/0172
    USPC ......................................................... 602/26
See application file for complete search history.

(56) References Cited

U.S. PATENT DOCUMENTS

| | | | | |
|---|---|---|---|---|
| 4,986,263 A | * | 1/1991 | Dickerson | A61F 5/0109 2/22 |
| 5,865,776 A | * | 2/1999 | Springs | A61F 5/0109 602/26 |
| 6,080,124 A | * | 6/2000 | Falk | A61F 5/34 602/23 |
| 6,551,264 B1 | * | 4/2003 | Cawley | A61F 5/0125 128/882 |
| 7,273,464 B2 | * | 9/2007 | Reinhardt | A61F 13/06 602/26 |
| 8,845,567 B2 | | 9/2014 | Herresthal | |

(Continued)

FOREIGN PATENT DOCUMENTS

| | | |
|---|---|---|
| DE | 8115670 U1 | 8/1981 |
| DE | 29803103 U1 | 6/1998 |

(Continued)

OTHER PUBLICATIONS

1st Office Action for Russian Patent Application No. 2015118314 dated Oct. 24, 2016.

(Continued)

*Primary Examiner* — Ophelia A Hawthorne
(74) *Attorney, Agent, or Firm* — Lucas & Mercanti, LLP

(57) ABSTRACT

A knee brace having a tubular elastic knitted body with at least one pressure pad arranged thereon, which, when the brace is being worn, extends across the patellar tendon. On the front side of the knitted body, a first tension strap is provided, which extends around only a certain part of the knitted body and passes over the pressure pad. On the rear side of the knitted body, a second tension strap is provided, which is offset in the height direction from the first tension strap, and which extends around only a certain part of the knitted body.

19 Claims, 4 Drawing Sheets

(56) References Cited

U.S. PATENT DOCUMENTS 9,545,328 B2 * 1/2017 Hess ................... A61F 5/30
2005/0203455 A1 9/2005 Cropper

FOREIGN PATENT DOCUMENTS

| DE | 20005661 U1 | 8/2001 |
| DE | 102008029825 A1 | 12/2009 |
| RU | 2007980 | 2/1994 |
| RU | 2011102594 | 7/2012 |

OTHER PUBLICATIONS

European Search Report dated Nov. 12, 2015 for European application EP 15166639.
German Office Action in copending German Patent Application No. 10 2014 107 239.1 dated Nov. 24, 2017 (5 pages).

* cited by examiner

KNEE BRACE

CROSS-REFERENCE TO RELATED APPLICATIONS

The present application claims priority of DE 10 2014 107 239.1, filed May 22, 2014, the priority of this application is hereby claimed and this application is incorporated herein by reference.

BACKGROUND OF THE INVENTION

The invention pertains to a knee brace, comprising a tubular elastic knitted body with at least one pressure pad arranged thereon, which, when the brace is being worn, extends across the patellar tendon.

Many people, especially athletes, often complain of pain in the knee. A syndrome which is frequently recognized in such cases is called "patellar apex syndrome". The patellar tendon is an essential part of the knee's locomotor apparatus. The patella is located on the front-facing side of the knee joint between the thigh and the lower leg. It is part of the knee joint and has a more-or-less triangular shape, wherein the apex of the triangle points down to the lower leg. The extensor muscles of the thigh are connected by a tendon to the top of the patella, that is, to the base of the triangle. From the apex of the triangle of the patella, the patellar tendon extends down to the anterior side of the lower leg. The force of the thigh extensor muscles is transmitted to the lower leg by the patellar tendon. The patellar tendon is a very narrow tendon, which must absorb and transmit all of this force. Especially under very heavy loads such as those which occur during rapid running or jumping, etc., the patellar tendon is subjected to strong and occasionally slightly jerky tensile stresses. This can cause excessive stress on the tendon, which then manifests as tendonitis.

Knee braces are used for the conservative treatment of this syndrome, i.e., of the pain; they consist of a knitted tube, which is elastic and therefore exerts a compressive force. A pressure pad is arranged on the knitted tube to exert the desired pressure on the patellar tendon. The pressure is intended to reduce the pain. So that the pressure pad exerts adequate pressure on the patellar tendon, a tension strap or tightening belt is provided. This strap may pass over the pressure pad, but in any case extends around to the back of the joint, i.e., to the hollow of the knee. It can therefore pass around a complete 360°, or it can extend at least from one side of the patella, around the back of the knee, to the other side of the patella. Although the tension strap is very important for applying the desired pressure, it can also be a problem, since it constricts the joint to a certain extent and thus interferes with the bending of the knee. The tension strap also increases the pressure on the back of the knee, which can sometimes be perceived as painful, which cancels out the advantages achieved in regard to the patellar tendon.

SUMMARY OF THE INVENTION

The invention is therefore based on the problem of providing a knee brace which is superior to the previously known type.

To solve this problem, it is provided according to the invention in a knee brace of the type described above that, on the front side of the knitted tube, a first tension strap is provided, which extends around only certain sections of the knitted tube and passes over the pressure pad; and that, on the rear side of the knitted tube a second tension strap is provided, which passes around only certain sections of the knitted body and is offset in the height direction from the first tension strap.

The knee brace according to the invention is characterized by two separate tension straps, which are arranged on opposite sides of the brace and which extend around only certain sections of the knitted tube. Both are important for adjusting the pressure on the pressure pad. The first tension strap extends directly over the pressure pad. Depending on how tightly the strap is pulled, a lower or a higher pressure can be exerted on the pressure pad. This first tension strap extends over only a certain section and only on the front side of the brace; therefore, when the first tension strap is tightened, the elastic knitting reacts by stretching, so that it can follow the force resulting from the tightening of the strap on the front side. The second tension strap extends across the rear side of the brace. It is offset in the height direction from the first tension strap, which—because it passes over the pressure pad resting on the patellar tendon—is diametrically opposite the back of the knee. The second tension strap is now is offset downward from that, preferably extending over the upper area of the calf. When this second tension strap is also tightened, a counter-pull acting against the first tension strap is created. The elastic knitting, which has followed the tightening of the first tension strap, is pulled back again by the second tension strap. As a result of these two tension straps, therefore, it is possible to build up the optimum pressure; that is, the pressure pad can be tightened onto the patellar tendon with the desired pressure. At the same time, the area of the knee joint is free of a tension strap, because the second tension strap, as described, is offset height-wise from the first and is preferably located in the area of the upper calf. Therefore, it has no effect on the bending of the knee, nor does it exert any pressure on the area of the hollow of the knee, which would be perceived as extremely uncomfortable.

The first tension strap should preferably extend around no more than 180°. This is already sufficient, since it is intended primarily to exert local pressure on the pressure pad. The second tension strap can also extend around a maximum of 180°, but, depending on the configuration of the brace, it can also pass around a somewhat larger or smaller angular range of the knitted tube. Its task is to produce a counter-pull sufficient to hold the brace in position on the rear side.

The distance between the two tension straps—relative to the longitudinal centerlines of the two straps—should be at least 4 cm, and preferably at least 5 cm. A distance of approximately 6 cm has been found to be especially effective. When the brace is being worn, the second tension strap, regardless of what this distance may be in the concrete case, extends below the first tension strap.

Each tension strap is preferably guided by two eyelets, wherein one end of the tension strap is attached to one of the eyelets, whereas the other end is looped through the other eyelet and can be held in the desired tensioning position by fastening means, especially by fastening means provided on the tension straps. Thanks to the guidance provided by these eyelets, the tension straps can be easily pulled tight and thus the brace held firmly in position. The eyelets are fastened to appropriate textile or plastic retaining tabs provided on the knitted tube. These retaining tabs can be parts of "appliqués", which are affixed to the sides of the knitted tube to form pockets extending in the lengthwise direction, into which stabilizing rods are inserted, as will be discussed in greater detail below.

The patellar tendon pressure pad, according to an effective elaboration of the invention, comprises a large knob on each side, pointing toward the interior of the knitted tube, between which several small projections are provided, which face toward the patellar tendon when the brace is being worn. The two large knobs, one on the right and one on the left, serve to anchor the pad in the recesses of the tibial plateau. By this means, the pressure pad can be encouraged to remain in position, keeping its lateral orientation. The central, preferably small knob-like projections exert pressure on the patellar tendon.

According to an especially effective elaboration of the invention, furthermore, a second pressure pad is arranged on the knitted tube; this pad is offset from the first pad in the height direction and, when the brace is being worn, is positioned above the patella. Pain is suppressed when the first pressure pad, i.e., the one assigned to the patellar tendon, is exerting pressure on the patellar tendon, but at the same time, if the pressure is high enough, the patella can be pushed slightly upward. This is sometimes felt to be unpleasant, i.e., the patellar tendon is stretched even more as a result. It is therefore especially advantageous to provide the second pressure pad, which, when the brace is being worn, is positioned above the patella and prevents the patella from be pushed upward out of position. The second pressure pad is therefore a counterpart to the first pad. The second pressure pad preferably has the shape of a horseshoe, so that it extends around the sides of the upper area of the patella; as a result, the patella is held with very good stability in the horseshoe-shaped pressure pad.

The first pressure pad and possibly the second pressure pad, if provided, are advisably accommodated in pockets provided on the knitted tube, wherein the pockets can be partially open, so that the pressure pads can be removed, if desired, and, if necessary, replaced by pads of a somewhat harder or softer material. Alternatively, the pockets can be closed on all sides, so that it is not possible to remove or to replace the pads.

The pocket or each pocket is preferably formed by means of a flat section, especially in the form of a knitted piece, which is attached to the knitted body. This flat section is provided on the inside surface of the knitted body and is therefore to be fabricated out of the softest possible material, possibly of a plush knit, to make the brace more comfortable to wear. Although it is possible to sew such a flat section in place, it is advisable to attach it by means of an adhesive, which is very easy to accomplish.

As previously described, it is conceivable that at least one, preferably two, stabilizing elements, especially in the form of elongated rods, could be arranged on the knitted tube; preferably two such elements, extending from the upper edge to the lower edge of the knitted tube, are provided. These slightly elastic webs stabilize the elongated, i.e., tubular, form of the knitted body, i.e., of the brace, so that it remains under tension in the longitudinal direction at all times. These rod-shaped stabilizing elements are preferably accommodated in pockets provided on the knitted tube, wherein, as previously described, appropriate flat sections or flat "appliqués" can be attached to the outside surface of the knitted tube. Again, these can be attached by means of an adhesive, or they can be sewn on, wherein the pockets are preferably closed. If the pockets are open, then it is possible to replace the stabilizing elements or to remove them. The previously described tabs, on which the eyelets are arranged, can be provided on these attached pieces.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

DETAILED DESCRIPTION OF THE INVENTION

Figure 1:
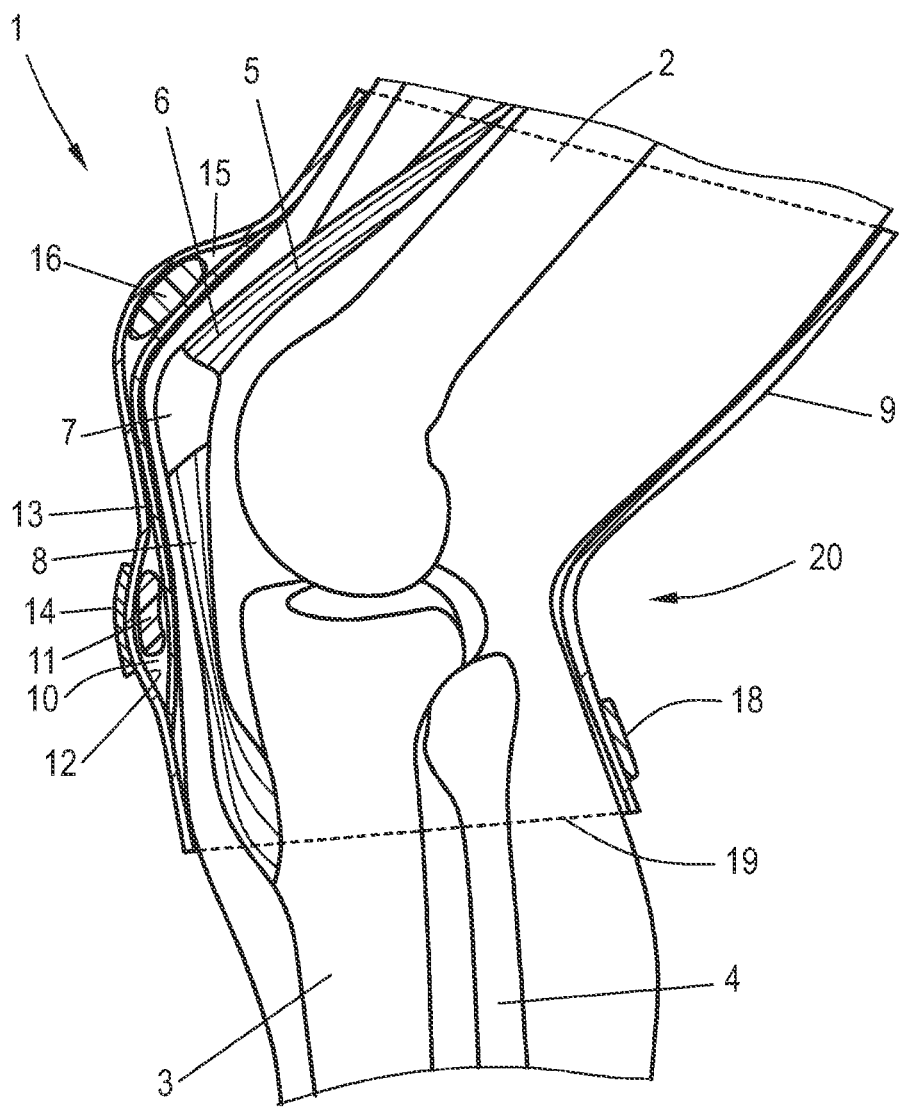
FIG. 1 shows a view of a knee joint with a cross section of a knee brace according to the invention arranged thereon.

FIG. 1 shows a schematic diagram of the human knee, on which a knee brace 1 according to the invention is arranged. Shown are the femur 2, the tibia 3, and the fibula 4. The quadriceps muscle 5 is connected by a tendon 6 to the patella 7, which for its own part is connected by the patellar tendon 8 to the tibia 3. Extending around the knee is the knee brace according to the invention. This knee brace consists of a tubular elastic knitted body 9, on the front side of which a first pocket 10 is formed, in which a pressure pad 11 is arranged, which, when the brace is being worn as in FIG. 1, extends transversely across the patellar tendon 8. The pocket 10 is formed by a flat section 13, consisting, for example, of a knitted or woven piece of fabric, e.g., terrycloth, attached to the inside surface 12 of the knitting. This flat section 13 can be attached by means of an adhesive, for example. Above the pressure pad 11, a tension strap 14 extends across the outside surface of the knitting; this strap can be pulled to adjust the pressure which the pressure pad 11 exerts on the patellar tendon 8, as will be discussed in greater detail further below.

A second pocket 15, furthermore, is formed on the tubular knitted body 9; a second pressure pad 16 is held in this pocket. As will be discussed again below, this pad is essentially in the form of a horseshoe, and, when the brace is being worn, it extends around the patella 7. This pocket 15, too, is formed by a flat section 13, which extends upward by an appropriate amount. The pressure pad 16 serves to prevent the patella 7 from being pushed upward as a result of the pressure being exerted on the patellar tendon 8 by the pressure pad 11.

On the rear side of the knitted body 9, a second tension strap 18 is provided, which has a downward offset from the first tension strap 14, i.e., is lower in the longitudinal direction of the tubular knitted body 9. The second strap is therefore positioned closer to the bottom edge 19 of the knitted body 9. As can be seen, it extends outside the area of the hollow of the knee 20 and extends over the upper area of the calf muscle. The distance between the tension straps—relative to their centerlines—should be about 6 cm, for example.

Figure 2:
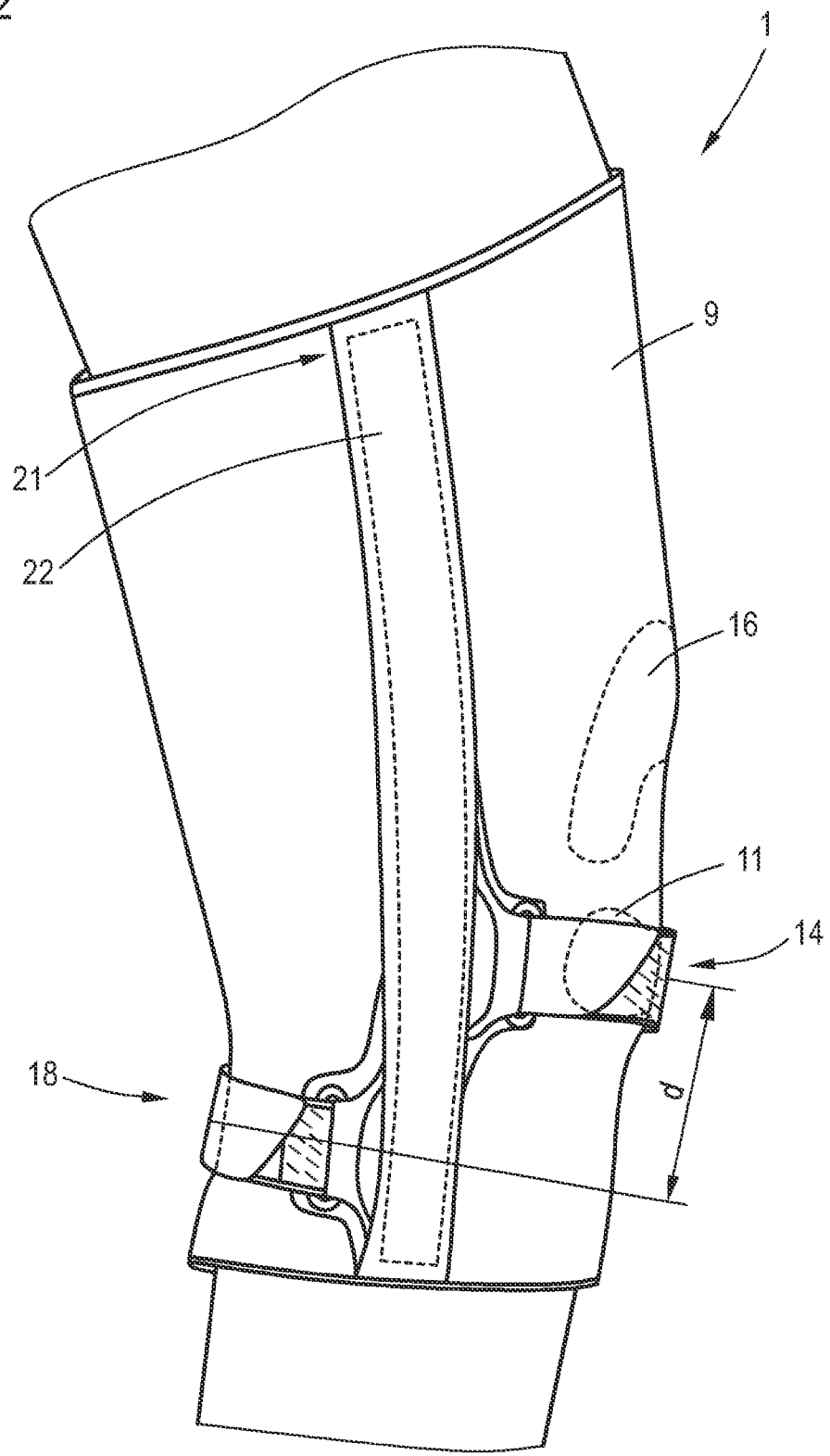
FIG. 2 shows a side view of the knee brace according to the invention.

Whereas FIG. 1 shows a more-or-less a cross-sectional view, FIG. 2 shows a side view of the applied knee brace 1 according to the invention. What is shown are the knitted body 9, the tension strap 14 extending across the front, and the tension strap 18 extending across the back. The first pressure pad 11, which rests on the patellar tendon 8, and the second, horseshoe-shaped pressure pad 16, which extends above and around the edges of the patella 7, are shown in dotted line. Also shown is the distance d in the longitudinal direction between the two tension straps 14 and 18. This distance d pertains to the distance between the centerlines of the straps. It should be at least 4 cm; it is preferably in the range of approximately 5-7 cm, and most preferably it is approximately 6 cm, based in each case on the geometry of the knee brace 1 before it has been put on.

On the outside surface of the knitted body 9, furthermore, a flat section 21 has been attached to form a pocket extending lengthwise along the knitted body 9. A rod-shaped stabilizing element 22, shown in dotted line, preferably an elastic rod, is accommodated in this pocket. A pocket like this is also formed on the opposite side of the knitted body 9 by a similar flat section; this means that a similar stabilizing rod is also provided on that other side. The two rod-like stabilizing elements 22 serve to keep the knitted body 9 stretched out in its elongated tubular form.

Figure 3:
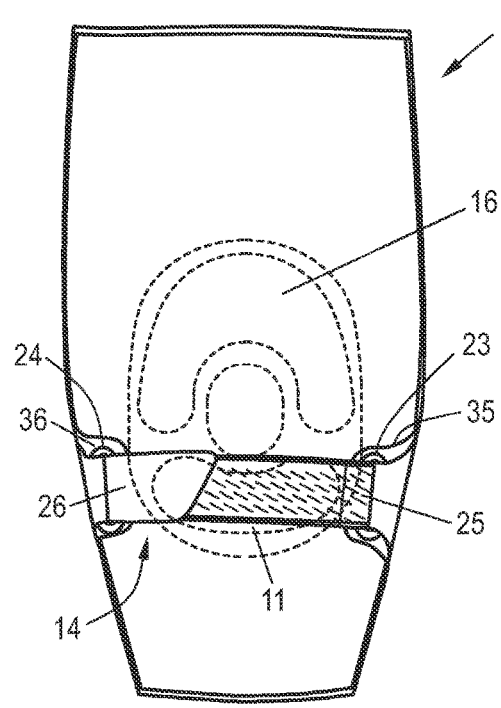
FIG. 3 shows a front view of the knee brace according to the invention with a closed tension strap.
Figure 4:
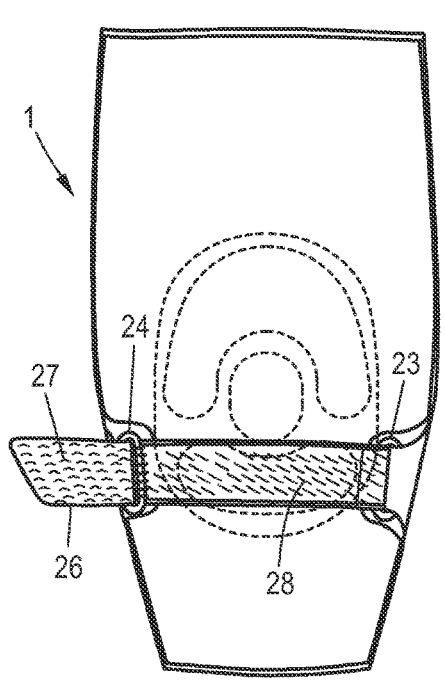
FIG. 4 shows the knee brace of FIG. 3 with an open tension strap.

FIGS. 3 and 4 show front views of the knee brace 1 according to the invention. What is shown is the closed first tension strap 14. The tension strap 14 is arranged on two eyelets 23, 24, wherein one end 25 of the strap is attached permanently to the eyelet 23, whereas the other end 26 is looped through the eyelet 24. In the area of the end 26 of the strap, a hook-type fastening section 27 is provided, whereas a loop-type fastening section 28 is applied to the top of the tension strap 14 in the area between the eyelets 24, 24. This makes it possible, when starting from the open position according to FIG. 4, to double over the end 26 of the strap and to fasten it in the desired, tensioned position by means of the hook-and-loop sections 27, 28. By pulling the tension strap appropriately through the eyelet 24, doubling it back, and then locking in the desired length, the knitted body 9 becomes slightly shorter, as can be seen. Because the tension strap 14 passes over the first pressure pad 11, pulling forcefully on the strap has the effect of adjusting the pressure exerted on the pressure pad 11, i.e., the pressure exerted via the pressure pad 11 on the patellar tendon 8.

Figure 5:
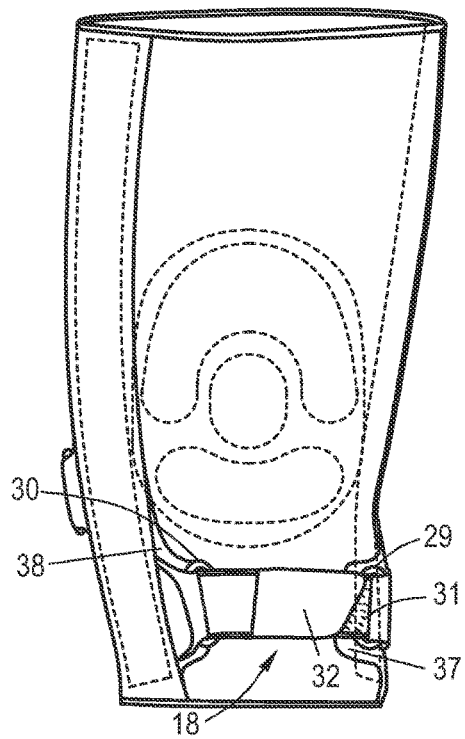
FIG. 5 shows a rear view of the knee brace of FIG. 3 with a closed tension strap.
Figure 6:
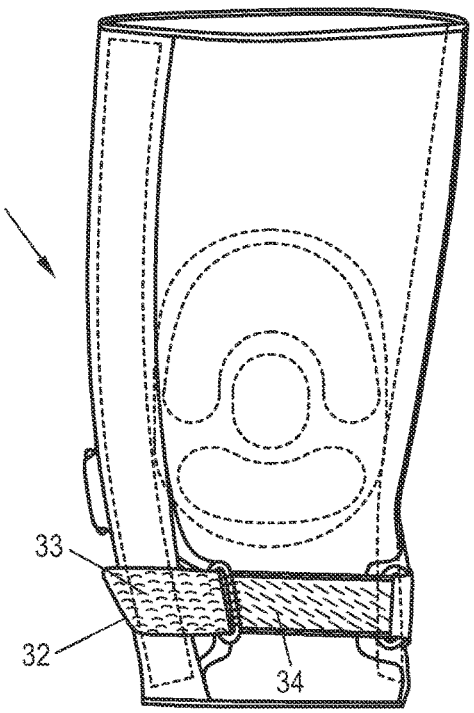
FIG. 6 shows a view of the knee brace of FIG. 5 with an open tension strap.

FIGS. 5 and 6 show the rear side of the knee brace 1 and the second tension strap 18 arranged on this side. This tension strap 18, too, is guided through two eyelets 29, 30, wherein one end 31 of the strap is permanently connected to the eyelet 29, whereas the other end of the strap is looped through the eyelet 30. This strap also comprises a hook section 33 at the end 32 and a loop section 34 in the adjacent strap area between the eyelets 29, 30. The way in which this functions is the same as described in relation to the first tension strap 14. That is, by pulling the tension strap through the eyelet 30 to the desired extent, doubling it back, and then fastening the strap in the pulled-through position by means of the hook-and-loop sections 33, 34, the desired tensioning position is set and can be held firmly in place. By means of this second tension strap 18, an opposing pressure, i.e., a counter-pull, to that produced on the other side of the brace can be created. For, as can be seen, the two tension straps 14 and 18 extend only across the area of their respective (front and rear) sides of the knee brace; that is, neither passes more than 180° around the knee. If only one tension strap is present, then, when it is pulled tight, the elastic knitted tube is tightened on only one side, whereas the opposite side merely stretches, so that it is impossible to build up sufficient pressure. By means of the second tension strap provided according to the invention on the opposite side, it is therefore possible to produce a corresponding counterpressure or counter-pull; that is, the elastic knitted tube is thus stabilized and can be stretched to only a small degree. The two tension straps 14 and 18 thus interact; that is, the local tensioning effect of the one is complemented by that of the other.

The pairs of eyelets 23, 24 and 29, 30 are arranged on tabs 35, 36 and 37, 38 of appropriate flexibility, which for their own part are attached to the knitted body 9; possibly, however, they could be parts of the flat sections 21, which are used to form the pockets extending in the lengthwise direction.

Figure 7:
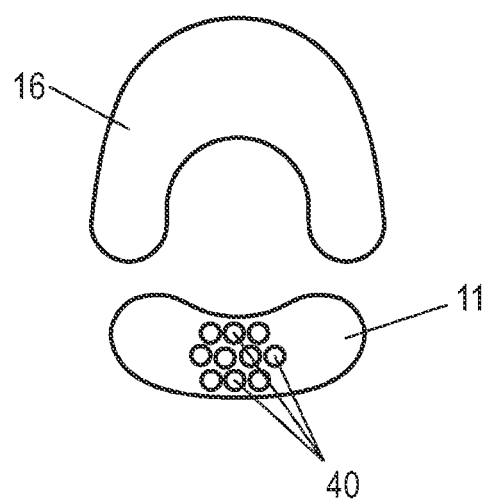
FIG. 7 shows a top view of the two pressure pads 11 and 16.
Figure 8:
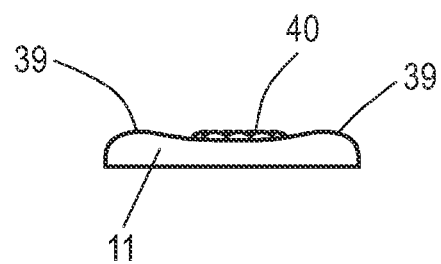
FIG. 8 shows a side view of the pressure pad 11.

FIG. 7 shows a top view of the two pressure pads 11 and 16. In its basic outline, the pressure pad 11 is slightly kidney-shaped. As shown in FIG. 8, it comprises two large lateral knobs 39, which, when the brace is being worn, face the patellar tendon 8 and lie laterally next to it, so that a certain lateral stabilization or fixation against lateral slipping-out-of-place is provided. In the area between the two large knobs 39, small knob-like projections 40 are formed, as clearly shown in FIGS. 7 and 8. These small knob-like projections, when the brace is being worn, lie directly above the pressure pad, so that, first, the tightening action results in the exertion of a global pressure on the pressure pad, and, second, the individual projections 40, spaced a certain distance apart, also exert a point-type pressure.

As FIG. 7 also shows, the second pressure pad 16 comprises the shape of a horseshoe. It is therefore able to extend around the top and sides of the patella 7; that is, the patella is prevented by this pressure pad 16 from being pushed upward. The two pressure pads 11 and 16 are made of a suitable plastic material comprising a certain flexibility or elasticity such as silicone.

While specific embodiments of the invention have been shown and described in detail to illustrate the inventive principles, it will be understood that the invention may be embodied otherwise without departing from such principles.

I claim:

1. A knee brace, comprising: a tubular elastic knitted body with at least one pressure pad, which is arranged thereon, the at least one pressure pad being configured to extend across a patellar tendon of a user when the brace is being worn; a first tension strap provided on a front side of the knitted body, so as to extend around only part of the knitted body and extend over the pressure pad covering the patella tendon; and a second tension strap provided on a rear side of the knitted body, the second tension strap being offset in a height direction from the first tension strap and extending around only part of the knitted body.

2. The knee brace according to claim 1, wherein a second pressure pad is provided on the knitted body and configured to be offset in the height direction from the first pressure pad so that the second pressure pad is positioned above the patella when the brace is worn.

3. The knee brace according to claim 2, wherein the first and the second pressure pad are accommodated in pockets provided on the knitted body.

4. The knee brace according to claim 3, wherein the pockets are formed by flat sections of knitted material attached to the knitted body.

5. The knee brace according to claim 4, wherein the flat sections are attached by an adhesive.

6. The knee brace according to claim 3, wherein the pockets are closed on all sides or are closed only partially.

7. The knee brace according to claim 2, wherein the second pressure pad is horseshoe-shaped.

8. The knee brace according to claim 1, wherein the second tension strap extends below the first tension strap and is at least 4 cm away from the first tension strap based on centerlines of the straps.

9. The knee brace according to claim 8, wherein the second tension strap is at least 5 cm away from the first tension strap.

10. The knee brace according to claim 9, wherein the second tension strap is at least 6 cm away from the first tension strap.

11. The knee brace according to claim 1, wherein the first tension strap is guided by two eyelets attached to the knitted body on opposing sides of the pressure pad, wherein a first end of the first tension strap is fastened to a first one of the eyelets and a second end is looped through a second one of the eyelets, and further comprising fastening means for holding the tension strap in a tensioning position.

12. The knee brace according to claim 11, wherein the fastening means are hook-and-loop elements provided on the tension straps.

13. The knee brace according to claim 1, wherein, on a side facing an interior of the knitted body, the pressure pad comprises large knobs on both sides, and several small projections between the large knobs, the small projections being directed toward the patellar tendon when the brace is worn.

14. The knee brace according to claim 13, wherein the projections are small knobs.

15. The knee brace according to claim 1, further comprising at least one stabilizing element arranged on the knitted body so as to extend from a top edge of the knitted body to a bottom edge.

16. The knee brace according to claim 15, wherein the stabilizing element is accommodated in a pocket provided on the knitted body.

17. The knee brace according to claim 1, wherein the first tension strap extends around at most 180° of the knitted body.

18. The knee brace according to claim 1, wherein the first tension strap is attached to the knitted body on opposing sides of the pressure pad.

19. The knee brace according to claim 1, further comprising stabilizing elements arranged on the knitted body so as to extend from a top edge of the knitted body to a bottom edge, and wherein the first tension strap and second tension strap are attached to the knitted body at the stabilizing elements.

* * * * *